United States Patent [19]

Oppong et al.

[11] Patent Number: 5,874,453

[45] Date of Patent: Feb. 23, 1999

[54] SYNERGISTIC ANTIMICROBIAL COMPOSITIONS CONTAINING A DIMETHYLAMIDE OF A CARBOXYLIC ACID WITH MIXTURE OF 2-(THIOCYANOMETHYLTHIO) BENZOTHIAZONE AND METHYLENEBIS (THIOCYANATE)

[75] Inventors: David Oppong; Vanja M. King, both of Memphis, Tenn.

[73] Assignee: Buckman Laboratories International, inc., Memphis, Tenn.

[21] Appl. No.: 893,552

[22] Filed: Jul. 11, 1997

[51] Int. Cl.$^6$ .................................................. A61K 31/425
[52] U.S. Cl. ......................... 514/367; 162/161; 514/515; 514/560
[58] Field of Search ..................................... 514/367, 515, 514/560

[56] References Cited

U.S. PATENT DOCUMENTS

| | | | |
|---|---|---|---|
| 3,306,810 | 2/1967 | Buckman et al. | 162/161 |
| 3,520,976 | 7/1970 | Buckman et al. | 424/270 |
| 3,524,871 | 8/1970 | Matt et al. | 260/454 |
| 4,268,403 | 5/1981 | Buckman et al. | 252/8.55 D |
| 4,425,186 | 1/1984 | May et al. | 162/158 |
| 5,073,638 | 12/1991 | Conaway et al. | 548/169 |
| 5,388,644 | 2/1995 | Romocki | 166/268 |

OTHER PUBLICATIONS

Chemical Abstracts (I) vol. 107:72869, 1987.
Chemica Abstracts (II) vol. 114:138026 s, 1991.

*Primary Examiner*—Leonard Schenkman
*Attorney, Agent, or Firm*—Armstrong, Westerman Hattori, McLeland & Naughton

[57] ABSTRACT

Compositions comprising a mixture of 2-(thiocyanomethylthio)benzothiazole and methylene-bis (thiocyanate) with dimethylamide of a carboxylic acid are disclosed which are synergistically effective compared to the respective components alone in controlling the growth of microorganisms in or on a product, material, or medium. Methods to control the growth of microorganisms and prevent spoilage caused by microorganisms with the use of the compositions of the present invention are also disclosed.

32 Claims, No Drawings

SYNERGISTIC ANTIMICROBIAL COMPOSITIONS CONTAINING A DIMETHYLAMIDE OF A CARBOXYLIC ACID WITH MIXTURE OF 2-(THIOCYANOMETHYLTHIO) BENZOTHIAZONE AND METHYLENEBIS (THIOCYANATE)

FIELD OF INVENTION

The present invention relates to certain compositions and processes useful for controlling the growth of one or more microorganisms and for preventing spoilage caused by bacteria, fungi, and algae in various products, materials, or media, particularly industrial products, materials, or media. These products, materials, or media include wood pulp, wood chips, lumber, adhesives, coatings, animal hides, paper mill liquors, process waters, pharmaceutical formulations, cosmetic and toiletry formulations, geological drilling lubricants, petrochemicals, agrochemical compositions, paints, leathers, wood, metal-working fluids, cooling water (e.g., cooling tower water), tanning liquors, starch, proteinaceous materials, acrylic latex paint emulsions, and textiles.

The novel compositions and processes incorporating the compositions of the present invention show unexpected, synergistic activity against microorganisms, including bacteria, fungi, and algae. Specifically, the present invention is directed to the use of compositions containing a) a mixture of 2(-thiocyanomethylthio)benzothiazole and methylenebis (thiocyanate) with b) a dimethylamide of a carboxylic acid.

BACKGROUND OF THE INVENTION

Many of the products, materials, or media referred to above, when wet or subjected to treatment in water, are susceptible to bacterial and/or fungal deterioration or degradation unless steps are taken to inhibit such degradation or deterioration. To control deterioration or degradation caused by microorganisms, various industrial microbicides are used but some of these biocides are of questionable utility because they have undesirable odors, are high in cost, show low degree of effectiveness or create hazards with respect to storage, use or handling.

For instance, the use of such popular industrial microbicides as organomercury compounds, organotin compounds and chlorinated phenols have come under great regulatory pressure in recent times because of their high toxicity and concern about their adverse effect on the environment. Workers in the trade have continued to seek improved biocides that have low toxicity and are capable of exhibiting a prolonged biocidal effect at normal use levels.

Methylene-bis(thiocyanate) can be used alone in low concentrations as low toxicity biocides. However, at low concentrations, methylene-bis(thiocyanate) tends to have a narrow antimicrobial spectrum and fails to completely prevent the growth of microorganisms.

Similarly, 2-(thiocyanomethylthio)benzothiazole (also known as TCMTB) can also be used alone in low concentrations as a biocide. Like the methylene-bis(thiocyanate), TCMTB at low concentrations, tends to have a narrow antimicrobial spectrum and fails to completely prevent the growth of microorganisms at times.

Accordingly, the present invention is directed to microbicidal compositions and processes incorporating these compositions that substantially obviate one or more of the problems, limitations, and disadvantages described above and experienced by those working in this art. In particular, the compositions of the present invention are capable of controlling the growth of at least one microorganism, especially fungi, bacteria, or algae, over prolonged periods of time and are safe and economical to use. The present invention is also directed to methods or processes of controlling the growth of at least one microorganism.

SUMMARY OF THE INVENTION

Accordingly, it is an object of the present invention to provide a microbicidal composition capable of controlling the growth of at least one microorganism, particularly fungi, bacteria, or algae, over prolonged periods of time.

It is an additional object to provide compositions which are economical to use. Methods of controlling the growth of at least one microorganism are also objects of this invention.

The present invention provides a composition to control the growth of at least one microorganism comprising a) a mixture of 2-(thiocyanomethylthio)benzothiazole and methylene-bis(thiocyanate) with b) a dimethylamide of a carboxylic acid where the components are present in a combined amount synergistically effective to control the growth of at least one microorganism. The compositions of the present invention preferably provide superior microbicidal activity at low concentrations against a wide range of microorganisms.

The present invention also provides a method for controlling the growth of at least one microorganism in or on a material or medium susceptible to attack by the microorganism which comprises the step of adding to the material or medium a composition of the present invention, where the components of the composition are present in synergistically effective amounts to control the growth of the microorganism.

The synergistically effective amount varies in accordance with the material or medium to be treated and can, for a particular application, be routinely determined by one skilled in the art in view of the present invention.

The present invention also embodies the separate addition of a mixture of 2-(thiocyanomethylthio)benzothiazole and methylene-bis(thiocyanate) with a dimethylamide of a carboxylic acid to the products, materials or media described above. According to this embodiment, the components are individually added to the system so that the final amount of the mixture of 2-(thiocyanomethylthio) benzothiazole and methylene-bis(thiocyanate), and the dimethyl amide present in the system at the time of use is that amount synergistically effective to control the growth of at least one microorganism.

The compositions of the present invention are also useful in preserving various types of industrial products, media, or materials susceptible to attack by microorganisms. Such media or materials include but are not limited to dyes, pastes, lumber, leathers, textiles, pulp, wood chips, tanning liquors, paper mill liquors, polymer emulsions, paints, paper and other coating and sizing agents, metalworking fluids, geological drilling lubricants, petrochemicals, cooling water systems, pharmaceutical formulations, and cosmetic and toiletry formulations.

The compositions of the present invention can also be useful in agrochemical formulations for the purpose of protecting seeds or crops against microbial spoilage. Additional advantages of the present invention will be set forth in part in the description which follows, and in part will be apparent from the description, or may be learned by the practice of the present invention. The advantages of the present invention may be realized and obtained by means of the elements and combinations particularly pointed out in the claims.

It is to be understood that both the foregoing general description and the following detailed description are exemplary and explanatory only and are not restrictive of the present invention as claimed.

DETAILED DESCRIPTION OF THE PRESENT INVENTION

According to the methods of the present invention, controlling or inhibiting the growth of at least one microorganism includes the reduction and/or the prevention of such growth.

It is to be further understood that by "controlling" the growth of at least one microorganism, the growth of the microorganism is inhibited and/or prevented. In other words, there is no growth or essentially no growth of the microorganism. "Controlling" the growth of at least one microorganism maintains the microorganism population at a desired level, reduces the population to a desired level (even to undetectable limits, e.g., zero population), and/or inhibits the growth of the microorganism. Thus, the products, material, or media susceptible to attack by these types of microorganisms are preserved from this attack and the resulting spoilage and other detrimental effects caused by the microorganism can be avoided. Further, it is also to be understood that "controlling" the growth of at least one microorganism can also include biostatically reducing and/ or maintaining a low level of microorganism such that the attack by a microorganism and any resulting spoilage or other detrimental effects are mitigated, i.e., the microorganism growth rate or microorganism attack rate is slowed down or eliminated.

When two chemical microbicides are combined or mixed into one product or added separately three results are possible:

1) The chemicals in the product produce an additive (neutral) effect.

2) The chemicals in the product produce an antagonistic effect, or

3) The chemicals in the product produce a synergistic effect.

An additive effect has no economic advantage over the individual components. The antagonistic effect would produce a negative impact. Only a synergistic effect, which is less likely than either an additive or antagonistic effect, produces a positive effect and therefore possesses economic advantages.

It is well-known in the microbicidal literature that there is no theoretical method to provide the likelihood of knowing, before actually testing, whether additive, antagonistic, or synergistic effects will be obtained when two biocides are mixed to yield a formulation. As can be seen in the examples, concentrations as high as 9000 ppm of the dimethylamide of a carboxylic acid by itself were ineffective against the test organism. Thus, the dimethylamide of a carboxylic acid for all practical purposes can be viewed as a non-microbicidal material. This is one of the unique features of this invention as it makes use of a non-microbicidal material such as dimethylamide to significantly improve on the antimicrobial properties of a mixture of 2-(thiocyanomethylthio)benzothiazole and methylene-bis (thiocyanate). This is a very unexpected and synergistic feature of this invention. This result, from a combination of microbicides and a non-microbicidal material, is a very rare occurrence.

The microbicidal compositions combining a mixture of 2-(thiocyanomethylthio)benzothiazole and methylene-bis (thiocyanate) with a dimethylamide of a carboxylic acid demonstrate an unexpected, synergistic effect compared to the respective components alone. Thus, these compositions achieve superior, i.e. greater than additive, microbicidal activity at low concentrations against a wide variety of microorganisms. Examples of microorganisms include fungi, bacteria, algae, and mixtures thereof such as *Trichodenna harzianum* and *Pseudomonas aeruginosa*. These organisms are some of the most common organisms associated with spoilage of products, materials, or media. Since these representative organisms are also some of the toughest organisms to control, the compositions of the present invention are believed to be effective against most bacteria, fungi, algae, and mixtures thereof. Preferably, the compositions of the present invention have a low toxicity.

The preparation of 2-(thiocyanomethylthio)benzothiazole is described in U.S. Pat. Nos. 3,520,976 and 5,073,638 and the preparation of methylene-bis(thiocyanate) (MTC) is described in U.S. Pat. No. 3,524,871, and these disclosures are fully incorporated by reference herein. 2-(thiocyanomethylthio)benzothiazole and methylene-bis (thiocyanate) are both commercially available and they are also easily synthesized from commercially available raw materials. MTC is also known as 2-methylene-bis (thiocyanate).

The 2-(thiocyanomethylthio)benzothiazole and methylene-bis(thiocyanate) mixture is sold in varying concentrations under such commercial names as Busan® 1009, MECT, etc. These commercial products are available from Buckman Laboratories International, Inc. and other distributors. Busan® 1009 is an emulsifiable concentrate of 10% by weight of 2-(thiocyanomethylthio) benzothiazole and 10% by weight of methylene-bis(thiocyanate). The amounts of the active ingredients in the mixture used as a component in this invention can preferably vary from about 1% to about 80%, preferably from about 1% to about 40%, by weight of 2-(thiocyanomethylthio)benzothiazole and from about 1% to about 80%, preferably 1% to about 40%, by weight of methylene-bis(thiocyanate). The most preferred amounts of these ingredients are those found in Busan® 1009.

A description of the dimethylamides of carboxylic acids can be found in U.S. Pat. Nos. 4,425,186 and 5,388,644, both incorporated in their entirety by reference herein. U.S. Pat. No. 5,388,644 further shows a method of making these types of dimethylamides. Suitable N,N-dimethylamides of carboxylic acids can be preferably prepared from straight chain carboxylic acids containing from 12–18 carbon atoms. Although any carboxylic acid containing from 12–18 carbon atoms is suitable for purposes of the present invention, those carboxylic acids containing 18 carbon atoms are preferred, since such acids are readily available in large quantities at economical costs. These preferred acids are further characterized by having at least one carbon-carbon double bond. Specific acids classified within this preferred category include, but are not limited to: oleic, linoleic, linolenic, ricinoleic, and mixtures thereof. Also suitable are the mixed acids found in tall, castor, corn, cottonseed, linseed, olive, peanut, rapseed, safflower, sesame, and soybean oils. A dimethylamide of tall oil fatty acids (DMATO) can be used and is available as a primary ingredient in Busperse® 47 dispersant, available from Buckman International Laboratories, Inc. A typical analysis of this tall oil fatty acid (which is converted to DMA) is as follows:

| | Typical Analysis |
|---|---|
| Fatty acid, pct | 97.5 |
| Rosin acids, pct | 1.0 |
| Unsaponifiables, pct | 1.5 |
| Linoleic acid, pct | 45.1 |
| Oleic acid, pct | 49.5 |
| Saturated acid, pct | 1.6 |
| Acid number | 195.0 |
| Saponification number | 197.0 |
| Color, Gardner | 3.0 |
| Specific gravity, 25° C./25 | 0.902 |
| Titre, °C. | 2.0 |
| Flash point, °F. | 380.0 |
| Fire point, °F. | 423.0 |

The N,N-dimethylamides of these tall oil fatty acids will sometimes hereinafter be referred to as DMA.

Specific examples of dimethylamides of a carboxylic acid include, but are not limited to, N,N-dimethyllinolenamide, N,N-dimethylricinoleamide, N,N-dimethyloleamide, and N,N-dimethyllinoleamide.

In accordance with the present invention, mixtures of dimethylamides of carboxylic acids can also be used in the composition of the present invention. The dimethylamides of carboxylic acids useful in the present invention are commercially available or may be synthesized from commercially available raw materials.

The dimethylamides of a carboxylic acid may be chosen, for example, based on the compatibility of the dimethylamide of the carboxylic acid with the products, materials, or media. The compatibility is readily determined by adding the dimethylamide of the carboxylic acid to the products, materials, or media to be used.

Compatibility may also be determined by criteria such as solubility in a fluid system and/or lack of reactivity with the fluid in question. When used in a fluid system, for example, it is preferable that the dimethylamide of a carboxylic acid be freely soluble or dispersible in the particular fluid system, resulting in a uniform solution or dispersion. Examples of fluid systems are tanning liquors, paper mill liquors, cooling tower waters, and paints.

In the following discussion of preferred embodiments, component (a) is a Busan® 1009 product which is an emulsifiable concentrate of a mixture of 10% by weight of 2-(thiocyanomethyl-thio)benzothiazole and 10% by weight of methylene-bis(thiocyanate) and component (b) is DMA. The DMA of choice is the N,N-dimethylamide of tall oil fatty acids.

As described above, components (a) and (b) are used in synergistically effective amounts. The weight ratios of (a) to (b) vary depending on the type of microorganisms, products, materials, or media to which the composition is applied. One skilled in the art can readily determine in view of this disclosure, and without undue experimentation, the appropriate weight ratios for a specific application. The ratio of component (a) to component (b) preferably ranges from about 99:1 to about 1:99, more preferably from about 1:30 to about 30:1, and most preferably from about 1:5 to about 5:1.

In general, an effective fungicidal, bactericidal, and/or algicidal response can be obtained when the synergistic combination is employed in concentrations (based on the media to be treated or emulsion used) ranging from about 0.01 to about 5000 ppm of the mixture 2-(thiocyanomethylthio)benzothiazole and methylene-bis (thiocyanate), preferably from about 0.1 to about 1000 ppm, and most preferably from about 0.1 to about 500 ppm; and from about 0.1 ppm to about 5000 ppm of the dimethylamide of a carboxylic acid, preferably from about 0.1 to about 2000 ppm, and most preferably from about 0.1 to about 500 ppm.

In accordance with the present invention, the composition may be in the form of a solid, dispersion, emulsion, or solution, depending upon the particular application. Further, the components of the composition may be applied separately or may be combined first and then applied to the product, material, or medium.

The present invention also provides a method for controlling the growth of at least one microorganism in or on a material or medium susceptible to attack by the microorganism which comprises the step of applying to the product, material, or medium a composition of the present invention, where the components of the composition are present in synergistically effective amounts.

Furthermore, the present invention provides a method of preventing spoilage of a product, material, or medium caused by a bacteria, fungi, and/or algae, comprising the step of applying to the product, material, or medium, a composition of the present invention where the components of the composition are present in synergistically effective amounts. For example, the composition may be used to prevent the spoilage of seeds or crops, e.g., cotton, barley, rice, maize, tobacco, etc.

Depending upon the intended use, the mode as well as the rate of application of the composition of this invention could vary. For instance, the composition could be applied by spraying or brushing onto the material or product. The material or product in question could also be treated by dipping in a suitable formulation of the composition. In a liquid or liquid-like medium, the composition could be added into the medium by pouring or by metering with a suitable device so that a solution or a dispersion of the composition could be produced. If used as a liquid preservative, for example, the composition may be prepared as an aqueous emulsion. If necessary, a surfactant may be added to the composition.

Based on the specific application, the composition may be prepared in liquid form by dissolving the composition in an organic solvent. The compositions of the present invention may be prepared in an emulsion form by emulsifying it in water, or if necessary, by adding a surfactant. In accordance with the present invention, additional components such as insecticides and the like may be added to the foregoing preparations without affecting the synergistic effects of the composition. Insecticides that may be used include, but are not limited to pyrethrins, nicotine, chlordane, and parathions.

The synergistic activity of the combinations described above has been confirmed using standard laboratory techniques as illustrated below. The following examples are intended to illustrate, not limit, the scope of the present invention.

Microbiological Evaluation

Nutrient broth (2.5 g/liter of deionized water) was prepared. This was distributed in 5 mL amounts into test tubes and autoclaved for 20 minutes at 121° C. After addition of the biocides in the desired concentrations to the nutrient broth, 100 microliters of a suspension of *Pseudomonas aeruginosa* cells of approximately $9.3 \times 10^8$ cfc/mL were added and incubated at 37° C. for 24 hours.

In the example which follows, synergistic effect was demonstrated in separate experiments by testing a mixture of 2-(thiocyanomethyl-thio) benzothiazole and methylene-bis (thiocyanate) or Busan® 1009, designated as component A and Busperse® 47 dispersant (DMA) as component B in a series of tests in varying ratios and a range of concentrations against the bacterium, *Pseudomonas aeruginosa* using the methods described above.

For each component A and B in a mixture containing A and B and for each component A and B acting alone, the lowest concentration which completely prevented growth of the bacteria for 24 hours was determined. These concentrations were used as end points for synergism calculations. End points for the components alone or in mixtures described above were then compared with the end points for the pure active ingredients alone in concomitantly prepared test tubes.

Synergism was demonstrated by the method described by Kull, E. C., Eisman, P. C., Sylwestrwicz, H. D., and Mayer, R. L. 1961. Applied Microbiology. 9: 538–541 wherein $QA/Qa + QB/Qb$ is less than 1

Qa=Concentration of compound A in parts per million, acting alone, which produced an end point.
Qb=Concentration of compound B in parts per million, acting alone, which produced an end point.
QA=Concentration of compound A in parts per million, in the mixture, which produced an end point.
QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the article by Kull et. al. Further information concerning this procedure is contained in U.S. Pat. No. 3,231,509, which disclosure is hereby made part of this application.

In general, however, an effective fungicidal and bactericidal response can be obtained when the synergistic combination is employed in concentrations ranging from about 0.01 to about 5000 ppm of the mixture of 2-(thiocyanomethylthio)benzothiazole and methylene-bis (thiocyanate), preferably from about 0.1 to about 1000 ppm, and most preferably from about 0.1 ppm to about 500 ppm; and from about 0.1 to about 5000 ppm of the dimethylamide of a carboxylic acid, preferably from about 0.1 to about 2000 ppm, and most preferably from about 0.1 to about 500 ppm.

As described already, synergistic activity results when the synergistic ratio of component (a) and component (b) is less than one. From the above examples, it is apparent that composition comprising a mixture of 2-(thiocyanomethylthio)benzothiazole and methylene-bis (thiocyanate) with a dimethylamide (which is a non-microbicide) in a synergistically amount possess effective antimicrobial activity to inhibit the growth of bacteria. It will be apparent for those skilled in the art that the required synergistically effective amounts (concentrations) will vary depending on the particular organisms and particular applications, and can readily be determined by routine experimentation. Use of a synergistically effective amount enables the use of a substantially smaller amount of the TCMTB and MTC to achieve a given effect than would be necessary for each biocide if used alone or than would be necessary if a mere additive effect from these two biocides were obtained.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

EXAMPLE 1

|  | $Q_a$ | $Q_A$ | $Q_b$ | $Q_B$ | $Q_A/Q_a$ | $Q_B/Q_b$ | $Q_AQ_a + Q_AQ_a$ |
|---|---|---|---|---|---|---|---|
| Pseudomonas aeruginosa | 10 | — | — | — | — | — | — |
|  | — | 5 | — | 0.90 | 0.5 | 0.00 | 0.50 |
|  | — | 5 | — | 2.3 | 0.5 | 0.00 | 0.50 |
|  | — | 5 | — | 4.5 | 0.5 | 0.00 | 0.50 |
|  | — | 5 | — | 9 | 0.5 | 0.00 | 0.50 |
|  | — | 5 | — | 23 | 0.5 | 0.00 | 0.50 |
|  | — | 5 | — | 45 | 0.5 | 0.00 | 0.50 |
|  | — | 5 | — | 90 | 0.5 | 0.01 | 0.51 |
|  | — | 5 | — | 225 | 0.5 | 0.03 | 0.53 |
|  | — | 5 | — | 450 | 0.5 | 0.05 | 0.55 |
|  | — | 5 | — | 900 | 0.5 | 0.01 | 0.6 |
|  | — | 5 | — | 1800 | 0.5 | 0.2 | 0.7 |
|  | — | — | >9,000 |  |  |  |  |

Component A = Busan 1009 (10% TCMTB/10% MTC)
Component B = Dimethylamide (DMA)
Test Organism Quantities producing endpoints (ppm)

What is claimed is:

1. A composition to control the growth of at least one microorganism comprising a synergistic microbicidally effective mixture of
   (a) a mixture of 2-thiocyanomethylthio(benzothiazole) and methylene-bis(thiocyanate), and
   (b) a dimethylamide of a carboxylic acid.

2. The composition of claim 1, wherein the microorganism is selected from bacteria, fungi, algae, or mixtures thereof.

3. The composition of claim 1, wherein said carboxylic acid contains 12–18 carbon atoms.

4. The composition of claim 1, wherein said carboxylic acid has at least one carbon to carbon double bond.

5. The composition of claim 1, wherein said carboxylic acid is a straight chain carboxylic acid containing 18 carbon atoms and at least one carbon to carbon double bond.

6. The composition of claim 5, wherein the straight chain carboxylic acid is linoleic acid or linolenic acid.

7. The composition of claim 5, wherein the straight chain carboxylic acid is oleic acid.

8. The composition of claim 5, wherein the straight chain carboxylic acid is ricinoleic acid.

9. The composition of claim 5, wherein the straight chain carboxylic acid is a mixture of acids derived from tall oil.

10. The composition of claim 5, wherein the straight chain carboxylic acid is a mixture of acids derived from linseed oil.

11. The composition of claim 5, wherein the straight chain carboxylic acid is a mixture of acids derived from cottonseed oil.

12. The composition of claim 5, wherein the straight chain carboxylic acid is a mixture of acids derived from corn oil.

13. The composition of claim 5, wherein the straight chain carboxylic acid is derived from peanut oil, tall oil, castor oil, corn oil, cottonseed oil, linseed oil, olive oil, rapseed oil, safflower oil, sesame oil, soybean oil, or mixtures thereof.

14. The composition of claim 1, wherein the dimethylamide of a carboxylic acid is N,N-dimethyloleamide.

15. The composition of claim 1, wherein the dimethylamide of a carboxylic acid is N,N-dimethyllinolenamide.

16. The composition of claim 1, wherein the dimethylamide of a carboxylic acid is N,N-dimethylricinoleamide N,N-dimethyllinoleamide, or N,N-dimethyloleamide.

17. The composition of claim 1, wherein the weight ratio of (a) to (b) is from about 99:1 to about 1:99.

18. The composition of claim 17, wherein the weight ratio of (a) to (b) is from about 1:30 to about 30:1.

19. The composition of claim 18, wherein the weight ratio of (a) to (b) is from about 1:5 to about 5:1.

20. The composition of claim 1, wherein the weight ratio of concentrations are from about 0.01 to about 5000 ppm of the mixture of 2-thiocyanomethylthio(benzothiazole) and methylene-bis(thiocyanate), and from about 0.1 to about 5000 ppm by weight of the dimethylamide of a carboxylic acid.

21. The composition of claim 20, wherein the weight ratio of concentrations are from about 0.1 to about 1000 ppm of the mixture of 2-thiocyanomethylthio(benzothiazole) and methylene-bis(thiocyanate), and from about 0.1 to about 2000 ppm of the dimethylamide of a carboxylic acid.

22. The composition of claim 21, wherein the weight ratio of concentrations are from about 0.1 to about 500 ppm of the mixture of 2-(thiocyanomethylthio)benzothiazole and methylene-bis(thiocyanate), and from about 0.1 to about 500 ppm of the dimethylamide of a carboxylic acid.

23. A method of controlling the growth of at least one microorganism in or on a product, material, or medium susceptible to attack by said microorganism comprising the step of applying to said product, material, or medium, a composition to control said growth comprising a synergistic microbicidally effective mixture of
  (a) a mixture of 2-(thiocyanomethylthio)benzothiazole and methylene-bis(thiocyanate), and
  (b) a dimethylamide of a carboxylic acid.

24. The method of claim 22, wherein the said product, material, or medium is wood pulp, wood chips, lumber, paints, leather, adhesives, coatings, animal hides, tanning liquors, paper mill liquors, metalworking fluids, petrochemicals, pharmaceutical formulations, cooling tower water, cosmetics, toiletry formulations, textiles, geological drilling lubricants or agrochemical compositions for crop or seed protection.

25. The method of claim 22, wherein said composition is in the form of a solid, dispersion, emulsion, or solution.

26. The method of claim 22, wherein said components (a) and (b) are added separately to the product, material or medium.

27. The method of claim 22, wherein said components (a) and (b) are first combined and then added to the product, material or medium.

28. The method of claim 22, wherein the weight ratio of concentrations are from about 0.01 to about 5000 ppm of the mixture of 2-(thiocyanomethylthio)benzothiazole and methylene-bis(thiocyanate), and from about 0.1 ppm to about 5000 ppm by weight of the dimethylamide of a carboxylic acid.

29. The method of claim 28, wherein the weight ratio of concentrations are from about 0.1 to about 1000 ppm of the mixture of 2-(thiocyanomethylthio)benzothiazole and methylene-bis(thiocyanate), and from about 0.1 to about 2000 ppm of the dimethylamide of a carboxylic acid.

30. The method of claim 26, wherein the weight ratio of concentrations are from about 0.1 to about 500 ppm of the mixture of 2-(thiocyanomethylthio)benzothiazole and methylene-bis(thiocyanate), and from about 0.1 to about 500 ppm of the dimethylamide of a carboxylic acid.

31. A method for preventing spoilage of a product, material, or medium, caused by bacteria, fungi, algae, or a mixture thereof comprising the step of applying to said product, material, or medium, a composition comprising a synergistic microbicidally effective mixture of
  (a) a mixture of 2-thiocyanomethylthio(benzothiazole) and methylene-bis(thiocyanate), and
  (b) a dimethylamide of a carboxylic acid.

32. The method of claim 28, wherein said material is seeds or crops.

* * * * *

UNITED STATES PATENT AND TRADEMARK OFFICE
CERTIFICATE OF CORRECTION

PATENT NO. : 5,874,453
DATED : February 23, 1999
INVENTOR(S) : David OPPONG and Vanja M, KING It is certified that error appears in the above-identified patent and that said Letters Patent is hereby corrected as shown below: On the title page, item [54] and in column 1, line 4 "Synergistic Antimcrobial Compositions" CONTAINING A DIMETHYLAMIDE OF A CARBOXYLIC ACID WITH MIXTURE OF 2-(THIOCYANOMETHYLTHIO)BENZOTHIAZONE AND METHYLEBIS(THIOCYANATE)" should read --SYNERGISTIC ANTIMICROBIAL COMPOSITIONS CONTAINING A DIMETHYLAMIDE OF A CARBOXYLIC ACID WITH A MIXTURE OF 2-(THIOCYANOMETHYLTHIO)BENZOTHIAZOLE AND METHYLENE-BIS(THIOCYANATE)--.

Signed and Sealed this

Twenty-second Day of June, 1999

Attest:

Q. TODD DICKINSON

*Attesting Officer*    *Acting Commissioner of Patents and Trademarks*